United States Patent [19]
Osman et al.

[11] Patent Number: 5,234,566
[45] Date of Patent: Aug. 10, 1993

[54] SENSITIVITY AND SELECTIVITY OF ION CHANNEL BIOSENSOR MEMBRANES

[75] Inventors: Peter D. J. Osman, West Lindfield; Bruce A. Cornell, Neutral Bay; Burkhard Raguse, St Ives; Lionel G. King, Marsfield, all of Australia

[73] Assignee: Australian Membrane and Biotechnology Research Institute Ltd., North Ryde, Australia

[21] Appl. No.: 654,635

[22] PCT Filed: Aug. 17, 1989

[86] PCT No.: PCT/AU89/00352

§ 371 Date: Apr. 18, 1991

§ 102(e) Date: Apr. 18, 1991

[87] PCT Pub. No.: WO90/02327

PCT Pub. Date: Mar. 8, 1990

[30] Foreign Application Priority Data

Aug. 18, 1988 [AU] Australia .................. PI9994

[51] Int. Cl.[5] .................................. G01N 27/26
[52] U.S. Cl. ..................... 204/403; 204/418; 204/416; 204/426; 435/817; 436/806
[58] Field of Search ............. 204/403, 418, 416, 426; 435/817; 436/806

[56] References Cited

U.S. PATENT DOCUMENTS

| | | | |
|---|---|---|---|
| 4,661,235 | 4/1987 | Krull et al. | 204/418 |
| 4,758,325 | 7/1988 | Kanno et al. | 204/418 |
| 4,776,944 | 10/1988 | Janata et al. | 204/403 |

FOREIGN PATENT DOCUMENTS

| | | |
|---|---|---|
| 4012385 | 3/1984 | Australia . |
| 0138150 | 10/1984 | European Pat. Off. . |
| 2195450 | 9/1987 | United Kingdom . |

OTHER PUBLICATIONS

"Ion-Channel Sensors", *Anal. Chem.*, Masao Sugawara, et al., 1987, 59, pp. 2842-2848.

"Chemical Modification of the Bilayer Lipid Membrane Biosensor Dipolar Potential" *Bioelectrochem. and Bioenergetics*, U. J. Krull, et al., 1986, 15, pp. 371-382.

"Voltammetric Studies of Electron-Conducting Modified Bilayer Lipid Membranes" *Bioelectrochem. and Bioenergetics*, Pawel Drysinski, et al., 1986, 16, pp. 185-191.

"Multisensing Ion-Selective Field-Effect Transistors Prepared by Ionophore Doping Technique", *Anal. Chem.*, Klara Bezegh, et al., 1987, 59, pp. 2846-2848.

"Chemical Derivatization of Microelectride Arrays by Oxidation of Pyrrole and N-Methylpyrrole: Fabrication of Molecule-Based Electronic Devices", *J. Am. Chem. Soc.*, Gregg P. Kittlesen, et al., 1984, 106, pp. 7389-7396.

"Dynamic and Steady-State Response of Electrochemical Detectors Based on Arrays of Small Electrodes", *Anal. Chem.*, L. Joseph Magee, Jr., et al., 1990, 62, pp. 2625-2631.

"Time and Spatial Dependence of the Concentration of Less Than $10^5$ Microelectrode-Generated Molecules", *Science*, Stuart Light, et al., vol. 243, pp. 1176-1178.

Primary Examiner—John Niebling
Assistant Examiner—Bruce F. Bell
Attorney, Agent, or Firm—Spensley Horn Jubas & Lubitz

[57] ABSTRACT

The present invention provides a biosensor comprising at least one lipid membrane, each membrane including at least one gated ion channel. The membranes comprise a closely packed array of self-assembly amphophilic molecules and the gated ion channel has a conductance which is dependent upon an electric field applied across the membrane. The biosensor of the present invention may comprise a plurality of discrete membranes each including at least one gated ion channel. The conductance of each of the membranes is measurable independently of the conductance of the other membranes.

38 Claims, 10 Drawing Sheets

SENSITIVITY AND SELECTIVITY OF ION CHANNEL BIOSENSOR MEMBRANES

FIELD OF THE INVENTION

The present invention relates generally to biosensors comprising membranes including at least one ion channel. In one form of the invention the conductance of the ion channels is dependent on electric field applied across the membrane. In addition, the present invention relates to biosensors comprising discrete arrays of membranes, each membrane including at least one ion channel, and the conductance of each membrane being measurable independently.

BACKGROUND OF THE INVENTION

It is known that amphiphilic molecules may be caused to aggregate in solution to form two or three dimensional ordered arrays such as monolayers, micelles, black lipid membranes, and vesicles or lisosomes, which vesicles may have a single compartment or may be of the multilamellar type having a plurality of compartments.

The selectivity and flux of ions through membranes can depend on the number, size and detailed chemistry of the pores or channels that they possess. It is through these pores or channels that permeating solute molecules pass across the membrane.

It is known that membranes may incorporate a class of molecules, called ionophores, which facilitate the transport of ions across these membranes. Ion channels are a particular form of ionophore, which as the term implies are channels through which ions may pass through membranes. The measurement of current flow across membranes due to a single ion channel is known and typically yields a current of 4 pA per channel.

The use of membranes including ion channels in biosensors has been proposed. In co-pending International Patent Application No. W089/01159 (published 9 Feb. 1989) the production of biosensors incorporating membranes including ion channels is disclosed. The disclosure of this application is hereby incorporated by way of cross-reference. The present invention seeks to provide biosensors of greater sensitivity.

DESCRIPTION OF THE PRESENT INVENTION

The present invention consists in a biosensor comprising at least one lipid membrane each membrane including at least one gated ion channel, each of said membranes comprising a closely packed array of self-assembling amphiphilic molecules, said at least one gated ion channel having a conductance which is dependent upon an electric field applied across the membrane.

In a preferred embodiment of this aspect of the present invention, the biosensor comprises a plurality of discrete lipid membranes, the conductance of each membrane being measurable independently of the conductance of the other membranes.

In a second aspect the present invention consists in a biosensor comprising a plurality of discrete membranes, each membrane including at least one gated ion channel, each of said membranes comprising a closely packed array of self-assembling amphiphilic molecules, the conductance of each of said membranes being measurable independently of the conductance of the other membranes.

As used herein the term "gated ion channel" is defined as an ion channel the passage of ions through which is dependent on the presence of an analyte.

As used herein the term "field effect ion channel" is defined as an ion channel in which the conductance of the ion channel is dependent on an electric field applied across a membrane incorporating the ion channel.

The amphiphilic molecules are normally surfactant molecules having a hydrophilic "head" portion and one or more hydrophobic "tails". Surfactants may be any of the known types, i.e. cationic (e.g. quaternary ammonium salts), anionic (e.g. organosulfonate salts), zwitterionic (e.g. phosphatidyl cholines, phosphatidyl ethanolamines), membrane spanning lipid, or non-ionic (e.g. polyether materials). The amphiphilic molecules are preferably such that they can be cross-linked. For this purpose it is necessary to provide the molecules with a cross-linkable moiety such as vinyl, methacrylate, diacetylene, isocyano or styrene groups either in the head group or in the hydrophobic tail. Such groups are preferably connected to the amphiphilic molecule through a spacer group such as described in Fukuda et al. J. Amer. Chem. Soc., 1986, 108 2321-2327.

Polymerisation may be performed by any of the known methods for polymerising unsaturated monomers, including heating with or without a free radical initiator, and irradiating with or without a sensitiser or initiator.

In a preferred embodiment of the present invention the amphiphilic molecules include or are decorated with at least one moiety cross-linked with at least one corresponding moiety on another of these molecules.

The ion channel used in the present invention is preferably selected from the group consisting of peptides capable of forming helices and aggregates thereof, podands, coronands and cryptands. However, it is presently preferred that the ion channel is a peptide capable of forming a helix or aggregates thereof.

Podands, cryptands and coronands have been described previously in the scientific literature (see, for example, V. F. Kragten et al., J. Chem. Soc. Chem. Commun. 1985, 1275; O. E. Sielcken et al. J. Amer. Chem. Soc. 1987, 109, 4261; J. G. Neevel et al., Tetrahedron Letters, 1984, 24, 2263).

Peptides which form $\alpha$ helices generally need to exist as aggregates in the membrane to form ion channels. Typically, the $\alpha$ helical peptides arranged to form aggregates in such a manner that an ion channel is created through the aggregate.

It is presently preferred that the ion channel is a peptide which forms a $\beta$ helix. An example of such a peptide is the polypeptide gramicidin A. This molecule has been the subject of extensive study (for further information see Cornell B. A., Biomembranes and Bioenergetics (1987), pages 655-676) The ion channel gramicidin A functions as a polar channel which traverses non-polar biological membranes. It is produced either synthetically or extracted from *Bacillus brevis*. In phospholipid bilayers gramicidin A is thought to exist as a helical dimer which substantially partitions into the hydrophobic region of the bilayer.

Further examples of molecules which may be used as ion channels in the present invention include gramicidin B, gramicidin C, gramicidin D, gramicidin GT, gramicidin GM, gramicidin Gm$^-$, gramicidin GN$^-$, gramicidin A' (Dubos), band three protein, bacteriorhodopsin, mellitin, alamethicin, alamethicin analogues, porin, tyrocodine, and tyrothricin.

Hereafter, the family of gramicidins will be referred to as simply gramicidin.

In the particular case of gramicidin, when the membrane is a monolayer, a monomer of gramicidin could be used as the ion channel. In a situation where the membrane is a bilayer, a synthetic analogue of dimeric gramicidin A could be used as the ion channel. In addition, where the membrane is a bilayer the ion channel may consist of two gramicidin A monomers, in which each monomer is in a different layer. In this situation the gramicidin A monomers are able to diffuse through the layers and when the two monomers come into alignment an ion channel is formed through the bilayer.

As stated above, the ion channel is gated. This may be done by a receptor moiety attached to, or associated with, an end of the ion channel, the receptor moiety being such that it normally exists in a first state, but when bound to an analyte exists in a second state, said change of state causing a change in the ability of ions to pass through the ion channel.

The first state of the receptor moiety will normally be a state in which the passage of ions through the ion channel is prevented or hindered. Attachment of the analyte to the receptor will thus cause the receptor to enter the second state wherein ions may pass through the ion channel. In this arrangement an ion channel may be used to detect as little as a single molecule of analyte the attachment of a single molecule of analyte will cause an ion channel to open and thus cause a leak of ions across the membrane. After a brief time this ion leak may be detected as the signal for the binding of the analyte to the receptor.

As would be readily appreciated by a person skilled in the art the alternative arrangement is when the receptor moiety is in the first state ions are able to pass through the ion channel and when in the second state the passage of ions through the ion channel is prevented or hindered. The receptor moiety may be any chemical entity capable of binding to the desired analyte and capable of changing the ion channel from its first state to its second state upon binding to that analyte. The receptor moiety is any compound or composition capable of recognising another molecule. Natural receptors include antibodies, antigens, enzymes, lectins, dyes and the like. For example, the receptor for an antigen is an antibody, while the receptor for an antibody is either an anti-antibody or, preferably, the antigen recognised by that particular antibody.

More details on gating mechanisms for ion channels are provided in co-pending International Application No. W089/01159.

Two mechanisms are known for the field dependence of conductance. One is the electrical potential profile along the ion channel. Secondly there is the possibility of conformational change in some ion channels when an electric field is applied. Thus with application of the field; polar, dipolar and polarisable groups may change orientation and distort the ion channel or change its potential profile thus influencing its transconductance. To make an ion channel with a transconductance that can usefully be modulated by an electric field it may be necessary to incorporate or remove highly polar, dipolar or polarisable groups on the ion channel. For example substitution of residues with a very low polarisability for the highly dipolar tryptophan rings in gramicidin A renders its conductance very potential dependent. Another gross example is Alamecithin which forms a hexameric ion channel when an electric field is applied.

The ion channels of the present invention can be modified by various residues, examples of which are given in Table 1 to achieve the required results.

TABLE 1 a) DIPOLAR GROUPS

Suitable derivatives of virtually any non-symmetric molecule, particularly those asymmetrically substituted with electron donating groups (e.g. alkoxyartl substituents), electron withdrawing groups (e.g. alkyl or ary carboxylic acids, aldehydes, ketones, nitriles or nitro compounds or combinations of these e.g. alkoxyntroryl derivatives; or charged dipolar species e.g. zwitterions, ylids.

b) POLAR GROUPS

Species bearing positive or negative charge (e.g. ammonium salts or carboxylates).

c) POLARISABLE GROUPS

Species containing highly polarisable electron clouds (e.g. halides, nitriles, sulfur derivatives, phosphorous derivatives, aryl, acetylenic or olefinic derivatives).

As would be apparent from the discussion above, the gated ion channels may be cross-linked with the amphiphilic molecules However, it is presently preferred that the gated ion channels are able to laterally diffuse through the membrane As will become clear from the following discussion the ability for the gated ion channels to laterally diffuse through the membrane results in greater sensitivity of the biosensor.

As stated above when the biosensor of the first or second aspect of the present invention comprises a plurality of discrete lipid membranes the conductance of each membrane is measurable independently of the conductance of the other membranes. The conductance of each membrane is preferably measured by (1) providing a separate high impedance measuring line to each membrane and/or (2) by multiplexing the membranes. It is presently preferred that where a large number of discrete membranes are used that the independent measurements are made by multiplexing the membranes and more preferably by serially multiplexing the membranes. Where multiplexing is used the multiplex lines are preferably low impedance excitation (or signal source) lines (held/clamped) at the excitation value; with a single high impedance current sensing line held at ground reference to complete the circuit for each element of the array when it is switched into circuit. While it is preferred that one current sensing line is used it will be recognised that more than one current sensing line may be provided. Either of these arrangements should result in a biosensor of optimal sensitivity.

Where the independent measurement of the conductance of the membranes is made using multiplexing it is preferred that the gated ion channels are field effect ion channels. It is also preferred that the plurality of discrete membranes including FEICs are arranged in a two dimensional array. It is presently preferred in this arrangement that the multiplex lines are driven from a complex signal such that in the two dimensional array each address line in one dimension has signal components which are cross modulated with the signals from address lines in the other dimension by the field effect ion channel.

In the biosensor of the present invention comprising a plurality of membranes including field effect ion channels, it is preferred that at least one dedicated electrode is provided on one side of each membrane which cooperates with an electrode on the other side of the membrane to enable the application of an electric potential across the membranes. It is preferred that each of these membranes is addressed by multiplexing the signal applied to the respective discrete electrodes.

As stated above biosensors made from ion channels incorporated in lipid membranes have been proposed. These typically consist of a lipid membrane containing an ion channel, which has been modified to change its ionic conductance when an analyte such as an antigen or antibody binds to it. Field effect ion channels (FEIC) can be used to improve these biosensors and their application involves the following principles:

1. Increasing the value of "Off" to "On" resistance improves the electrical signal to noise ratio in a gated ion channel biosensor.
2. The probability that in a given period of time the molecule will react with the sensor for a given volume of analyte depends on the area of the sensor.
3. A non linear conductance can be used to improve the sensor signal to noise.

In this application the ratio of "off" to "on" resistance can be increased and shunt capacitance is reduced without increasing the time it takes for a molecule to diffuse to the sensor. Additionally field effect ion channels can be used to create a distinctive transduction signal. These techniques can be used to greatly enhance the sensitivity and selectivity of the biosensor.

The sensitivity of a biosensor, such as that described in Patent Application No. WO 89/01159 is dependent in part on the ratio of ion channel resistance to lipid membrane resistance, i.e. the "on" to "off" resistance of the ion channel incorporated in the lipid membrane. If the ratio of lipids to ion channels is too large, then the sensor's electrical impedance can be so low that impedance changes due to a sensing event are difficult to detect. Similarly if the absolute number of ion channels is too high then the sensors electrical impedance is lowered, by leakage currents through the ion channels if they are normally blocked, or by the ion channel intrinsic conductance if they are normally open.

To improve the sensitivity one can reduce the number of ion channels and reduce the sensor surface area in order to increase the signal response to the minimum number of binding events. However, a reduced surface area implies a longer time for the analyte to diffuse to the point of sensing, and for small concentrations a reduction in probability of detection. The alternative method, using flow through techniques, may not be suitable because of the small analyte volumes involved in high sensitivity tests (e.g. one droplet), and because of noise generated by the analyte flow perturbing the membrane.

A method proposed here is to set up an array of small area sensors and to switch between them so as to move the point of sensing in the analyte. The switching can be done with a conventional electronic multiplexer, although for two dimensional arrays at least half the address lines would need to have a high impedance. Alternatively it can be done using FEIC's as part of the sensing ion channel, in which case it is possible to switch between sensing elements in a two dimensional array using low impedance lines and one common high impedance line as described in one of the following examples.

Diagnostic reliability can be improved by using a variety of functionally different tests and by measuring the statistics for sets of functionally identical tests. In both of these cases the ability to scan an array of biosensors is useful and both approaches require the availability of a mechanism for switching between biosensors.

A second method for improving sensitivity involves the use of FEIC gated ion channel biosensors which are designed with a conductance characteristic which can be readily distinguished from interfering signals such as the lipid membrane conductance and this method will also be discusses in the following examples.

BRIEF DESCRIPTION OF THE DRAWINGS

In order that the nature of the present invention may be more clearly understood preferred forms thereof will now be described with reference to the following examples and accompanying Figures in which.

DETAILED DESCRIPTION OF THE INVENTION

Example 1

Ion Channels with Field Modulated Transconductance

Polar groups can be incorporated into many parts of an ion channel structure for the purpose of transconductance modulation. By way of example ion channels may be employed with polar, dipolar or polarisable residues located: at the head region of the ion channel, on the side chains of the ion channel and at the dimeric junction of an ion channel dimer.

In general the mechanisms for transconductance modulation can be direct modification of the potential profile, distortion of the channel by a conformational change or modification of the potential profile by a conformational change.

It will usually be more appropriate to measure the transconductance of such ion channels using a pulse signal or AC signal. This keeps the advantages of high signal bandwidth, avoids unwanted electrochemical effects and allows higher field strengths than a bilayer could withstand in a DC signal.

Example 2

An Ion Channel with a Field Modulated Head Group

Figure 1C:
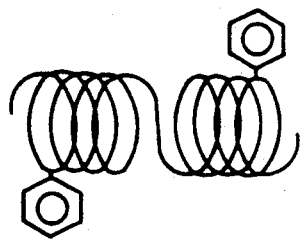
FIG. 1 shows schematically field modulated ion channels, in which "A" shows modulated head groups; "B" shows modulated side chains; and "C" shows polymeric ion channel.
Figure 1B:
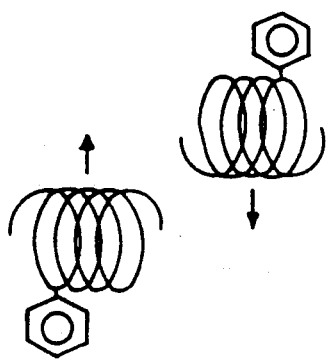
Figure 1A:
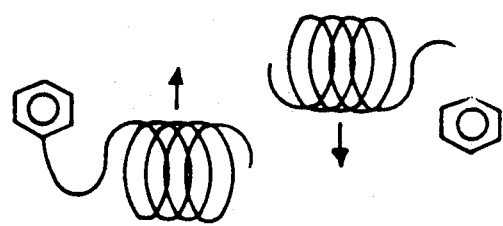

In this case polar, dipolar or polarisable residues are attached directly or via linker groups to the mouth of the ion channel in the region of the surrounding lipid head groups (FIG. 1a). These ion channels can then be incorporated into either lipid monolayers or bilayers or can be laid down as a secondary film in series connection with a monolayer or bilayer already containing ion channels.

This form of ion channel is not as sensitive as those of Examples 3 and 4 because of the surrounding highly polar electrolyte molecules which attenuate field strength in the head group region.

If the ion channel is held in a lipid bilayer then it is also possible to use opposite polarity polar groups on each side of the bilayer to enhance sensitivity.

Example 3

An Ion Channel with Field Modulated Side Chains

In this form of ion channel polar, dipolar or polarisable residues are attached as side chains to the ion channel so that they lie within the low permittivity region of the lipid membrane (FIG. 1b). Examples are given in Table 1.

Example 4

A Field Modulated Polymeric Ion Channel

This form of ion channel is used where monomers (e.g. alamethicin or gramicidin) are combined to form an ion channel. The monomers are chemically or physically linked and contain polar, dipolar or ionised groups as described previously. A field is applied which may assemble, distort or disrupt the ion channel thus modulating its ion conductance FIG. 1(c) shows a dimer with dipolar residues attached as side chains. Distortion of the dimer by the electric field force acting on the dipolar groups may modulate the dimer transconductance by inducing conformational changes in the region of the dimeric bond.

Example 5

An Array of Biomolecular Switches Using Field Modulated Ion Channels

Figure 2:
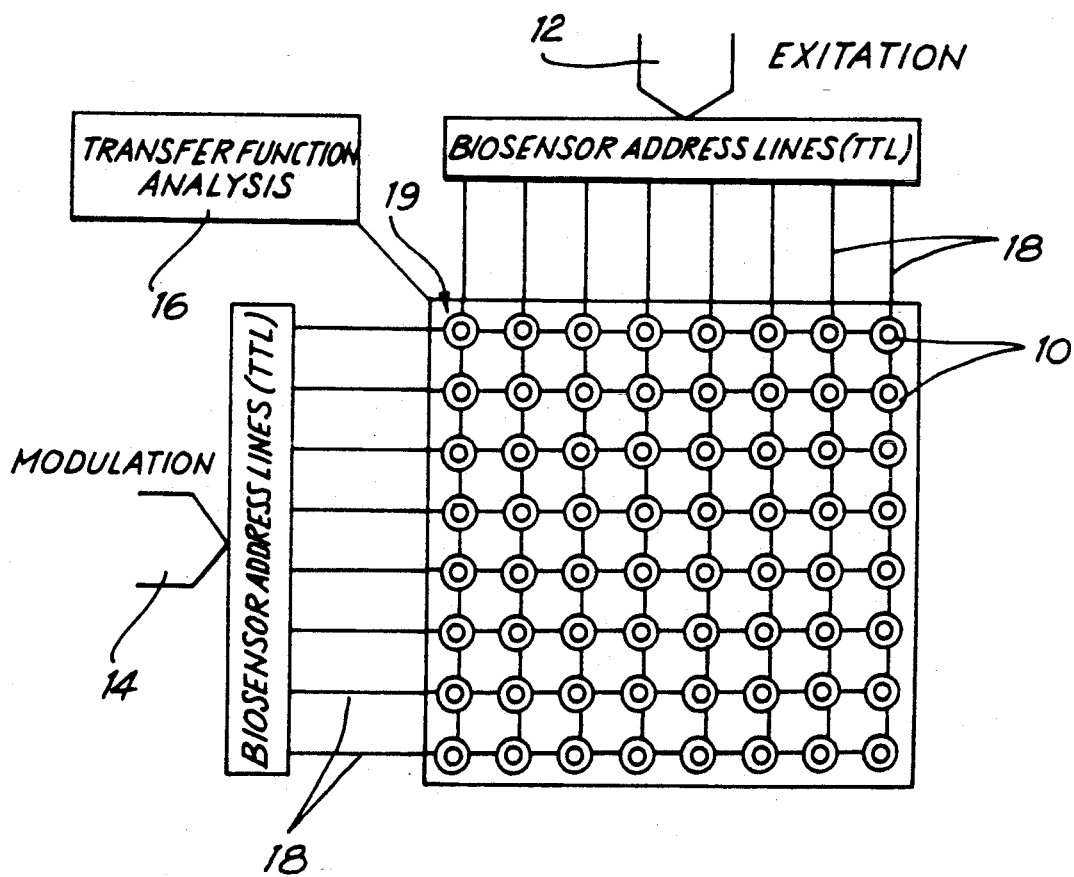
FIG. 2 shows a schematic representation of a low impedance biosensor multiplexer.

Arrays of field effect ion channels may find application wherever it is desirable to control ion flow. In particular, applications may exist in biosensors, or chemical analysis techniques such as electrophoresis.
  a. A one dimensional array of field effect ion channels could be addressed using a single common high impedance signal sensing electrode and a separate low impedance signal sensing electrode for each channel.
  b. A high density of ion channels could be addressed using a two dimensional array in which each side of the ion channel is addressed by separate electrodes. In this case at least half the address lines should be high impedance to reduce cross modulation. Problems with fabrication and signal bandwidth may arise because of this high impedance
  c. A high density of ion channels can be addressed by a two dimensional array in which one side of the channel is connected to an electrode which is capacitively or resistively connected to two address lines. Address lines are used as low impedance sources of signals which cross modulate when applied to a non-linear transfer point such as the non-linear conductance of the FEIC. Thus, by switching between the modulating electrodes separate elements on the array can be addressed. (FIG. 2). A single high impedance measuring electrode only is required.

FIG. 2 shows schematically a low impedance biosensor multiplexer comprising an array of membranes including gated ion channels 10, an excitation source 12, a modulation source 14, a transfer function analyser 16 an array of address lines 18, and a common sensing line 19.

Because the address lines are on the same side of the channel, and because the signal is well labelled, they can carry low impedance signals without the problems of cross modulation which would exist if they were on opposite sides. For the technique to work it is essential that the ion channel have a distinctive transconductance characteristic which can be modulated, hence the necessity to use FEIC's. The address electrodes can be AC or DC coupled.

In the fabrication of a two dimensional array of FEIC's a pattern of electrodes and resistors or capacitors is formed by etching a multilayer substrate of alternately electronically conducting and insulating materials. This substrate is then coated with a monolayer or bilayer of lipid. The lipid membrane can be formed directly on some substrate surfaces; alternatively it can be formed on a hydrogel coating over the substrate. Ideally the interconnecting resistors and conductors will be insulated from the lipid material while the electrodes are electronically coupled to the membrane either directly or by capacitive coupling. Ideally the membrane will be divided into electrically isolated array elements. This may be achieved by making wells over each element of the array.

Suitable materials for a substrate may be silicon and its oxides and nitrides, the metals (particularly palladium or platinum), the glasses, ceramics and oxides (particularly aluminium oxide and the titanates and zirconates), the conducting polymers such as nafion, and polypyrrolle, and the insulating polymers used in integrated circuit and capacitor production such as parylene, polyvinylidene fluoride, polyester and polypropylene.

Suitable materials for the lipid would be the phospholipids, such as DMPC and DPPC, which are relatively stable. If the lipid is directly coating a metal surface such as palladium, then it would be necessary to substitute a thiol residue such as a sulfhydryl for the phospholipid headgroup.

In use the array would be placed in a liquid or hydrogel electrolyte containing a common high impedance electrode which is connected to the signal analysis equipment. If very low frequency or DC signals are being used then it may be necessary to use an additional reference electrode to balance the electrochemical potential at the signal electrodes. The signal analysis can use a variety of techniques such as: spectral analysis, cyclic voltammetry, noise analysis, dynamic impedance analysis or statistical analysis. All these methods and preferably carried out in conjunction with the decoding mechanism which is used as described below, to distinguish between interference and true signals and to distinguish between sensing elements.

Example 6

A Bionsensor Using an Array of Field Modulated Ion Channels

It is well known that arrays of biosensors would be useful for multifunctional testing. However, as described above, some forms of biosensor array can also be used to improve sensitivity, selectivity, time response and reliability.

A biosensor could be constructed, using for example an array of gated ion channel biosensors made from a field effect ion channel. An appropriate field effect ion channel is given in Example 3. Any of the switching methods described in Example 8 could be used to address the individual elements, although those described for 1 dimensional arrays would be more appropriate for small arrays and those described for 2 dimensional arrays more appropriate for large arrays. The signal analysis methods described in Examples 5 and 8 can be combined to provide an effective addressing and detection algorithm. The reliability of detection could be further enhanced by measuring from many elements for statistical analysis.

Example 7

Ion channels with non linear conductance characteristics with electric field are known to exist.

The conductance of a lipid bilayer is known to be much less non linear with electric field than some of these ion channels.

Biosensors can be proposed based on the use of modified ion channels in lipid membranes.

Lipid membranes are known to present a significant shunt impedance to ion channels thus making it difficult to distinguish ion channel conduction activity from lipid conduction.

A method for increasing the sensitivity of a biosensor based on ion channels in a lipid membrane may be to use ion channels which have been modified to have an electric field dependent conductance. A complex waveform is applied to the biosensor and compared with those frequency components of the resulting signal which result from the non linear transfer function of the ion channel.

An example would be to apply an excitation voltage synthesised from two sine waves to one side of the biosensor membrane and to use a phase lock loop to measure the frequency difference component, in the current passing through the biosensor.

Let "V" represent the excitation voltage and "A" represents the current passing through the biosensor. If "f1" and "f2" represent the frequencies of the two sine waves in the excitation signal and if they are respectively the n1 and n2 sub-harmonics of a fundamental sinewave "f0" then the detected current signal can be represented as $A\{(1/n1 - 1/n2) \times f0\}$. Lipid membranes can have a conductance which varies by a factor of approximately 2 over the usable range of excitation signal whereas an ion channel can be modified to act as a biosensor with a highly non linear conductance which can vary by as much as 50. Thus the ion channel would tend to have a higher level of crossmodulation of the excitation sine waves when compared to the membrane and the improvement in discrimination would be:

$$\frac{A\{(n1 - n2) \times f0\} \text{ ion channel}}{A\{(n1 - n2) \times f0\} \text{ membrane}}$$

If the dynamic state of biosensor impedance is being measured, for example a change in the statistics of the period of gating following a biochemical reaction, then the difference frequency of the above example should be greater than the Nyquist frequency for the shortest pulse period considered significant in the analysis.

Other signal processing strategies for biosensors based on a nonlinear ion channel are:
Spectral analysis
Cyclic voltammetry with excitation from either current or voltage sources
Noise analysis
Dynamic impedance analysis
Statistical analysis Other modalities for discriminating ion channel from lipid membrane conductance are: optical and/or acoustic excitation of the ion channel.

Example 8

It is known that as the area of a membrane increases, the sensitivity of a system to measure ion channel activity is reduced because the membrane shunt resistance and capacitance grows while that of the ion channel remains constant.

To measure low concentrations of ion channel activity, cell areas of from 0.1 to 100 micron$^2$ are typical.

If the limiting sensitivity is defined as the conductance of a single channel divided by total conductance of the sensor then the dependence of limiting sensitivity on area of such a system can be expressed in terms of functions of: the area of the ion channel "f1(Ai)", the membrane area "f2(Am)", and the area of ion leakage at the membrane perimeter F3(Ae) as:

$$1/(1 + f2(Am)/f1(Ai) + f3(Ae)/fi(Ai))$$

The functions of f1 and f2 are, to a first approximation, linear, giving admittance per unit area. However, f3 is a more indeterminate function giving leakage admittance around the biosensor cell perimeter. In a circular cell it is approximately proportional to $(Rm^2 - Re^2)$ where Rm is the radius of the biosensor and Re is the radius to the region where edge leakage occurs.

If a biosensor detects by binding analyte molecules of cross sectional area "Aan" to a few ion channels which are consequently opened or closed, then if there are N1 ion channels which can laterally diffuse through the membrane then the limiting sensitivity is given as:

$$\frac{Am}{Aan} \times \frac{1}{1 + N1 + f2(Am)/f1(Ai) + f3(Ae)/fi(Ai)}$$

For a system in which the channels are evenly distributed but cannot laterally diffuse, the sensitivity limit as given as:

$$\frac{1}{Aan} \times \frac{N1}{1 + N1 + f2(Am)/f1(Ai) + f3(Ae)/fi(Ai)}$$

It can be seen that the advantage of a membrane which is large compared to the analyte molecule, is offset by the limiting effect of Am on electrical sensitivity. It can also be seen that simply increasing the number of ion channels overcomes this problem in systems with anchored ion channels, however, it does make detection more difficult because the ability to characterise ion channel activity by spontaneous changes in the conduction of individual channels, f1(Ai), is lost in the average conduction signal. However, if the membrane and its ion channels are divided into N2 adjacent but electrically isolated and independently measured regions, then the limiting sensitivity becomes:

"Laterally Diffusing"

-continued $$\frac{Am}{Aan} \times \frac{1}{1 + N1/N2 + f2(Am)/(N2 \times f1(Ai)) + SQRT(N2) \times f3(Ae)/f1(Ai)}$$

or

"Anchored"
$$\frac{Am}{Aan} \times \frac{N1}{1 + N1/N2 + f2(Am)/(N2 \times f1(Ai)) + SQRT(N2) \times f3(Ae)/f1(Ai)}$$

By this means the electrical sensitivity can be greatly increased by reducing the limiting effect of membrane area on electrical sensitivity, and by retaining the information contained in single ion activity while allowing more ion channels to be used. The increased number of ion channels will also increase time response by reducing the lateral diffusion times. Improved sensitivity and time response in a biosensor, based on an ion channel in a lipid membrane can be achieved by independently sensing a number of small cells distributed over the active surface area, by multiplexing or by parallel amplification or both.

Biosensors based on field effect ion channels which have been modified may also be multiplexed.

The speed of response and sensitivity of the biosensor described above are optimal when a system of parallel amplifiers is used on an array of close packed cells. A serially multiplexed system with close packed cells will be equally sensitive as the parallel system but will have a longer time response which improves with the number of parallel signal paths in the network. Spacing the sensing elements and multiplexing between them will result in an improvement in response time but a loss of sensitivity proportional to the ratio of the sensor area/sensing area.

The biosensors described below typically use a 2 or 3 terminal bridge connected to a gated ion channel modified in the membrane. Preferably multiplexing is carried out entirely by excitation electrodes with the high impedance sensing electrode(s) not being associated directly with the multiplexor.

(1) One Dimensional Array (a) The independent measurements are set up as parallel high impedance ($10^{10}$ ohms) amplifiers. 10,000 are required for ultimate sensitivity and time response in a 1 cm$^2$ sensor with close packed 100 micron$^2$ cells.

(b) The independent measurements are set up as 10,000 serially multiplexed cells. Multiplex lines are low impedance with a single current sensing line held at ground reference. Response time is typically between 20 and 200 seconds. Sensitivity is optimal.

(c) A mix of serial multiplexed and "N" parallel signal paths is used. The response time is reduced proportionally to the N amplifiers required for each path. Note the amplifiers have to be independent and therefore isolated at high impedance from each other.

(2) Two Dimensional Array (a) As in 3 above, however, ion channels with non linear conduction are used and the multiplexer lines are driven from a complex signal (typically "N" paired frequencies Vn(f1) and Vn(f2)) so that frequency division demultiplexing of the different frequencies corresponding to each parallel path can be carried out. Thus the time response in 2 above is reduced by "N" in a system with one high impedance line.

(b) As for 4 but where the multiplexer electrode on the membrane substrate is coupled to excitation sources via a resistor network so that two signal lines can be used to address the electrode in a two dimensional array.

(c) System as for all above biosensors but where the membranes are not close packed. This reduces the time response and/or sensitivity but for many applications this would be a useful configuration.

Example 9

1) Improved Sensitivity in a Non Linear Sensor

This example describes a device for enhancing sensitivity in a biosensor based on a gated ion channel in a lipid bilayer.

Figure 3A:
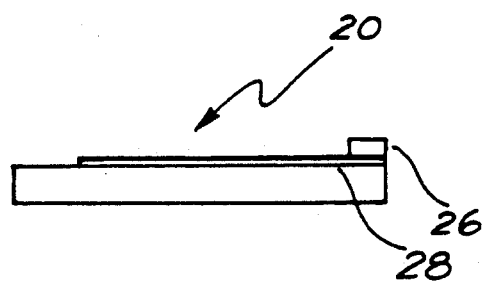
FIG. 3 shows a metal or glass electrode in which "A" is a side view and "B" is a view from above.
Figure 3B:
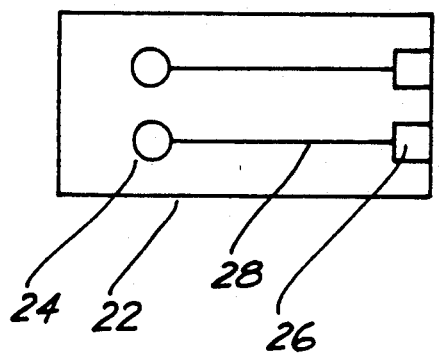

FIG. 3 shows schematically metal on glass electrodes 20 from the side (A) and from above (B). The metal on glass electrodes 20 consists of a glass substrate 22, active electrodes 24, connector pads 26 and electrical connections 28 connecting connector pads 26 with electrodes 24. The electrical connections 28 and active electrodes 24 are sputtered layers.

A glass sheet 22, such as a microscope slide, is prepared by cleaning in solvent, water and chromic or nitric acid, but not detergent. Connector pads 26 are electroplated as per FIG. 3 and the electrode 20 is then cleaned with distilled deionised water and by ethanol vapour degreasing or in a soxhlet extractor.

It is then quickly dried in a clean dust-free atmosphere with a jet of pure dry nitrogen obtained for example from liquid nitrogen boil off and transferred to a sputtering apparatus containing multiple targets of chromium, and either gold, palladium or platinum. The sputtering chamber should be protected from diffusion pump vapour by a liquid nitrogen cold trap. A sputter coating of 100 angstroms of chromium, followed by 200 angstroms of gold, palladium or platinum, is deposited by shadow masking the pattern given in FIG. 3. This pattern shows two active electrodes 24, although both are not always required it is useful to have one electrode without biosensing material to act as a reference. The electrodes 24 should then be immediately coated with lipid by adsorption or Langmuir Blodgett dipping as described in the steps to prepare a biosensor given in International Patent Application No. WO 89/01159.

This form of biosensor uses a combination of bound alcohol and lipid as an insulator. The shadow mask creates a penumbral region of electrically discontinuous metal around the perimeter of the metallisation, which serves to anchor lipid support material and allow a well insulating membrane to surround and cover the electrically continuous region. Shadow masking is preferred because it avoids the chemical contamination associated with photolithography. If photolithography is used then the cleaning process described above should be repeated after the normal post photolithography cleaning procedures have been followed.

Figure 4:
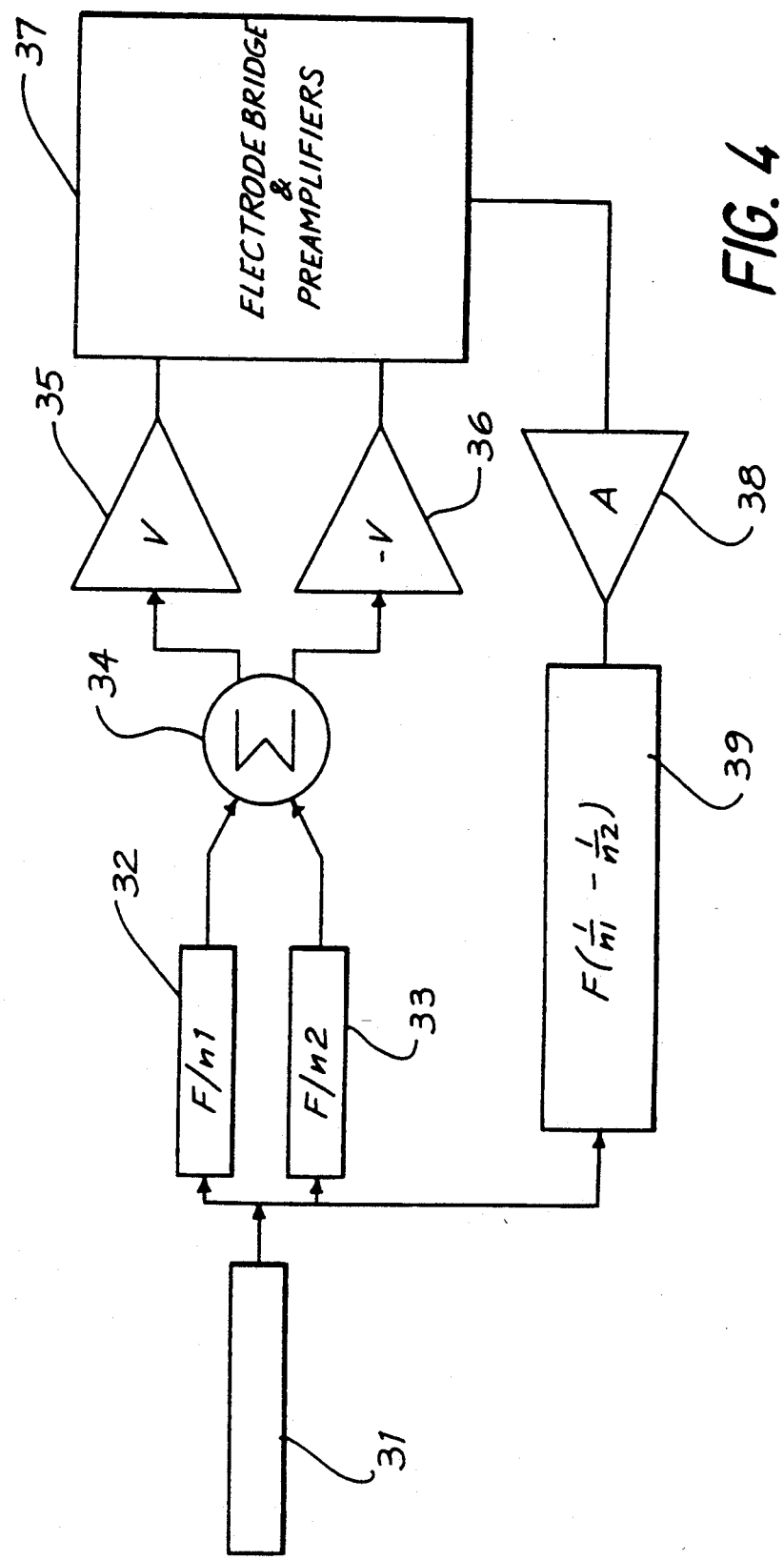
FIG. 4 shows a schematic representation of an impedance bridge system.
Figure 5:
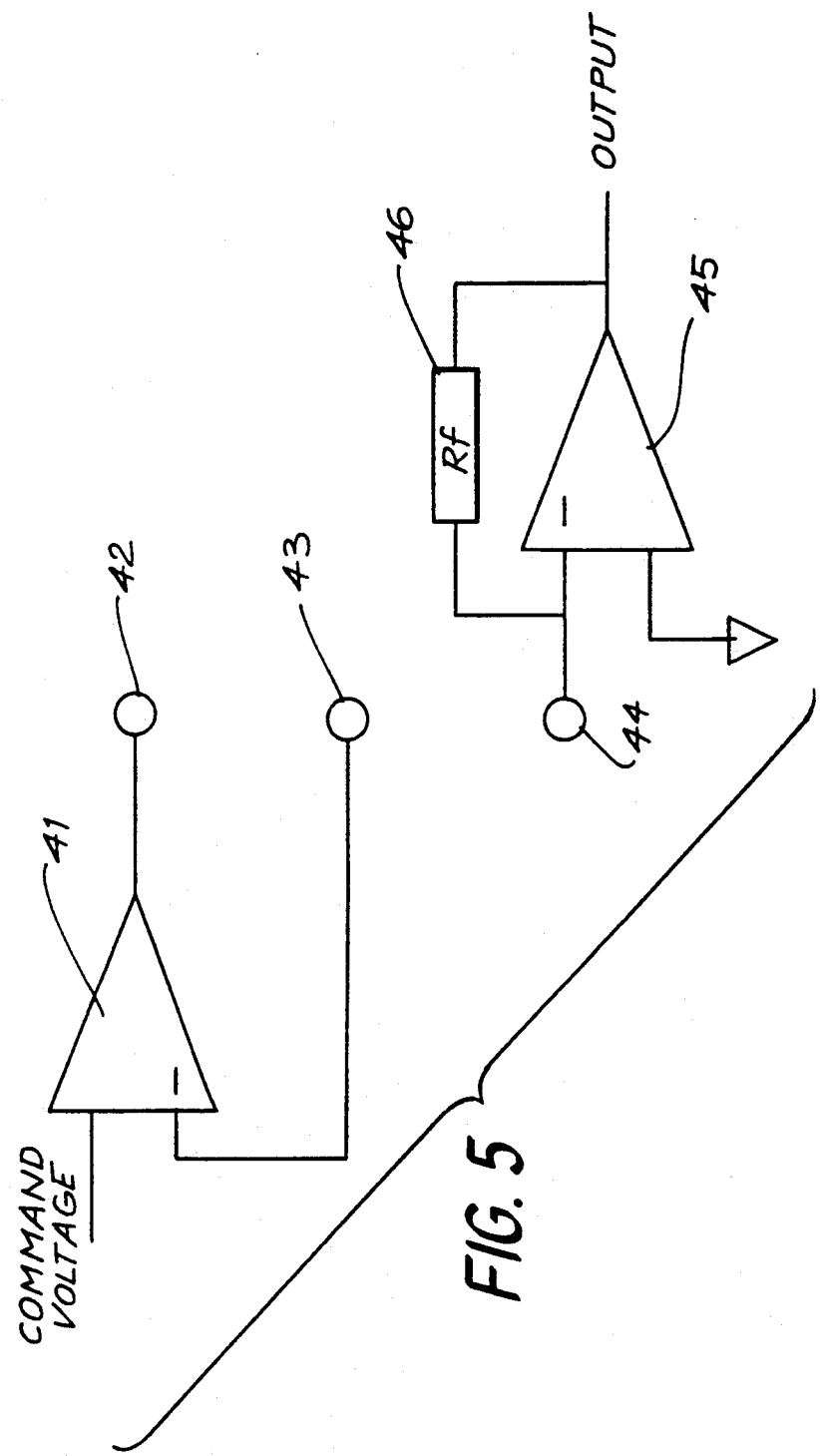
FIG. 5 shows a schematic representation of a three terminal bridge.
Figure 6:
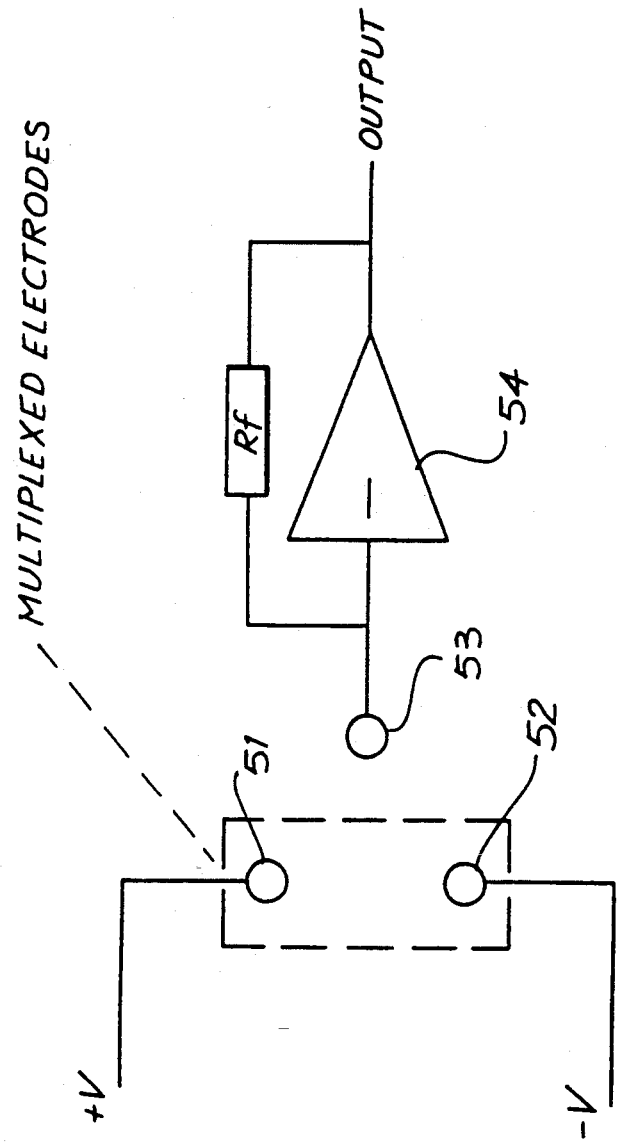
FIG. 6 shows a schematic representation of a balanced voltage impedance bridge.

A suitable electronic system for analysis is given in FIG. 4. Three forms of preamplifier are shown: FIG. 5 shows a standard voltage clamp amplifier, FIG. 6 shows a balanced voltage bridge for measuring differential impedance with a biosensor containing two active electrodes. Both elements are coated in lipid but only one includes the biosensing gated ion channels.

FIG. 4 shows an example of a method to measure ion channel impedance in a membrane by using the non-linear conductance property of the ion channel. FIG. 4 shows a local oscillator 31 which might typically run at 10 kHz. Frequency dividers 32 and 33 derive signals of frequency F/n1 and F/n2 from the local oscillator 31. Typically n1=10 and n2=11. A summing amplifier 34 adds the two signals from frequency dividers 32 and 33, whilst buffer amplifiers 35 and 36 supply a signal to the sensing electrode. Buffer amplifier 36 also inverts the signal so that it is the opposite polarity to the signal from buffer amplifier 35, however, this inverted signal is only required where the preamplifier used is as shown in FIG. 6. The system for switching (multiplexing) the signal to an array of electrodes and sensing the resultant signal with a single current sensing amplifier is shown generally as 37 and described in more detail in FIGS. 5, 6 and 7. The sensed signal is then further amplified by an amplifier 38 and the component of the signal with a frequency of (F/n1 - F/n2) is detected and amplified by a phase lock loop detector 39. Because this signal component results from the non-linear conductance of the ion channel it can be used to preferentially distinguish changes in the ion channel conductance from the rest of the membrane impedance which has a relatively linear conductance.

Figure 7:
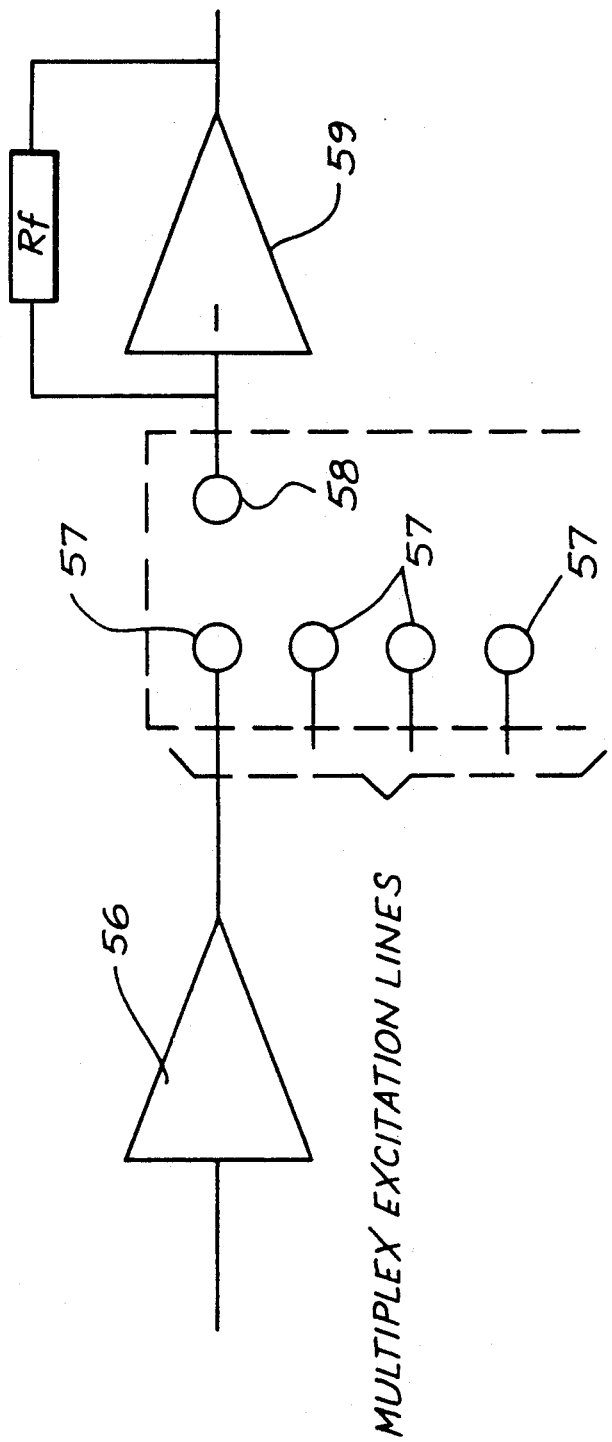
FIG. 7 shows a schematic representation of a two terminal bridge.

FIGS. 5, 6 and 7 show forms of preamplifiers suitable for use with the sensors described in the examples. FIG. 5 shows a preamplifier which is more suitable for single sensors; while FIGS. 6 and 7 show preamplifiers which are more readily used with an array of sensors.

The preamplifier shown in FIG. 5 is a standard three terminal impedance bridge comprising an amplifier 41 which supplies enough current to counter electrode 42 so that a reference electrode 43, is always held at the same potential as the command voltage. The reference electrode 43 is connected to a high impedance negative feedback input of amplifier 41 so that it accurately monitors the potential of the electrolyte solution and controls the current to the counter electrode so that the electrolyte solution is clamped to the same potential as the command voltage. The active electrode 44 is coated with the membrane and held at a zero value of potential so that current must flow into it from the counter electrode 42 dependent on the impedance of the membrane. The amplifier 45 measures this current by forcing it through a resistor 46. Thus the conductance of the membrane coating the active electrode 44 can be determined from the measured value of the potential of the electrolyte and the current passing through the membrane.

The preamplifier and electrode arrangement shown in FIG. 6 comprises a balanced bridge consisting of an electrode 51 which is coated with the lipid membrane containing gated ion channels and an electrode 52 which is coated with a lipid membrane only. The two electrodes are supplied with signals which are identical but opposite in polarity so that if the electrode conductances are equal there is a zero potential in the electrolyte in which they are both immersed. A sensor electrode 53 measures imbalances in the potential of the electrolyte so that if the conductance of the electrode 51 was altered by a biosensor reaction (i.e. opening or closing of the gated ion channel) then the change in potential would be sensed by electrode 53 and amplified by a high impedance amplifier 54. Electrodes 51 and 52 can be a pair in an array of such pairs which can be addressed by switching the excitation signal to them.

The preamplifier shown in FIG. 7 represents a two terminal impedance bridge in which an amplifier 56 supplies an excitation signal to an electrode 57, which is coated with a membrane. Electrode 57 is one of an array of electrodes and the excitation signal can be switched to each electrode in the array. An electrode 58 detects the current passing through electrode 57 and amplifies it with a high impedance amplifier 59. Thus the conductance of an array of electrodes such as 57 can be measured.

2) Improved Sensitivity and Response Time in a Multiplexed Sensor

Methods are described for a biosensor and measuring system which allows multiplexing to enhance the performance of the gated ion channels in lipid membrane sensor described in International Patent Application No. WO 89/01159.

The biosensor is fabricated using a combination of silicon integrated circuit technology and lipid coating methods.

Figure 8:
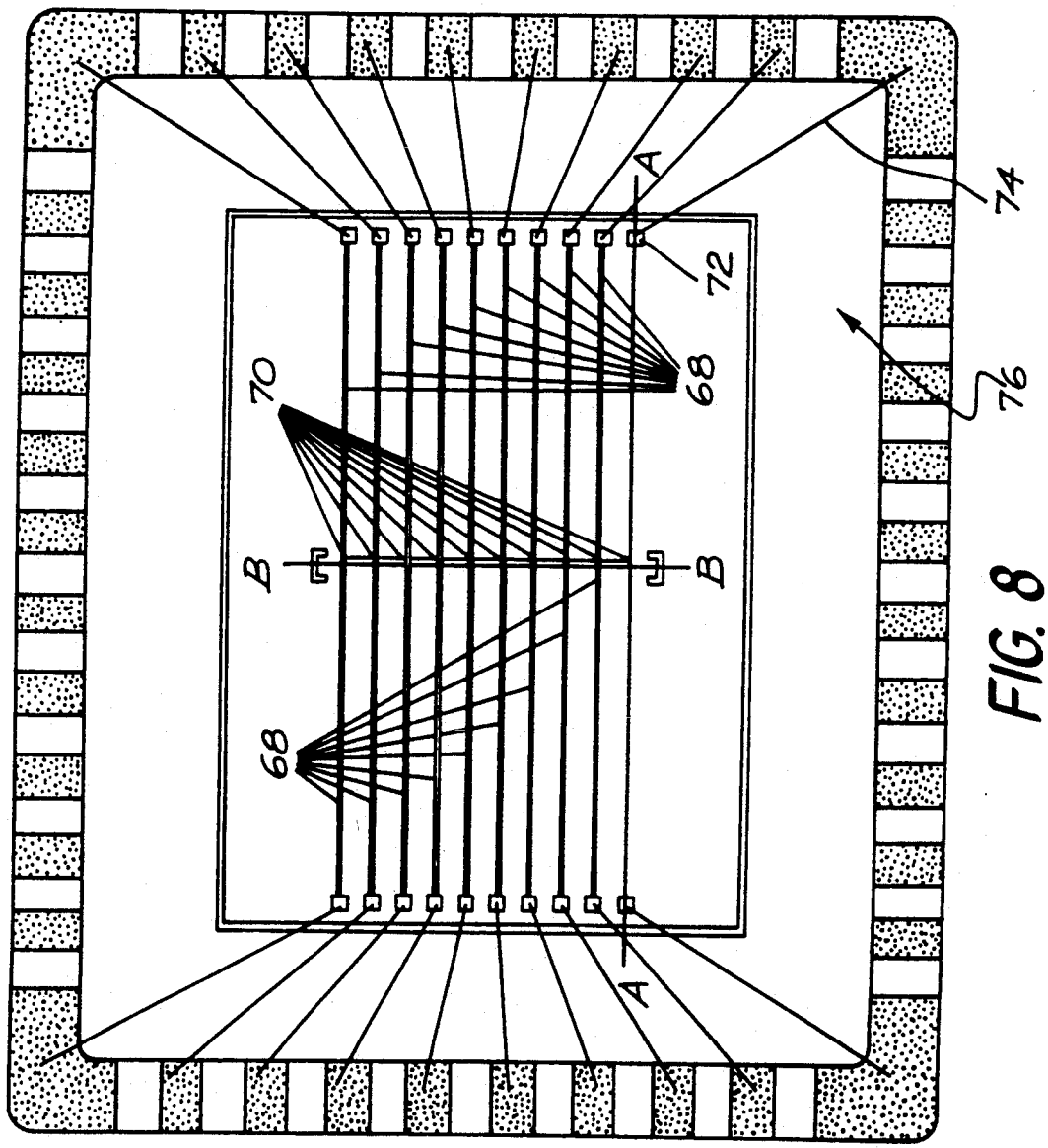
FIG. 8 shows a biosensor chip.
Figure 9:
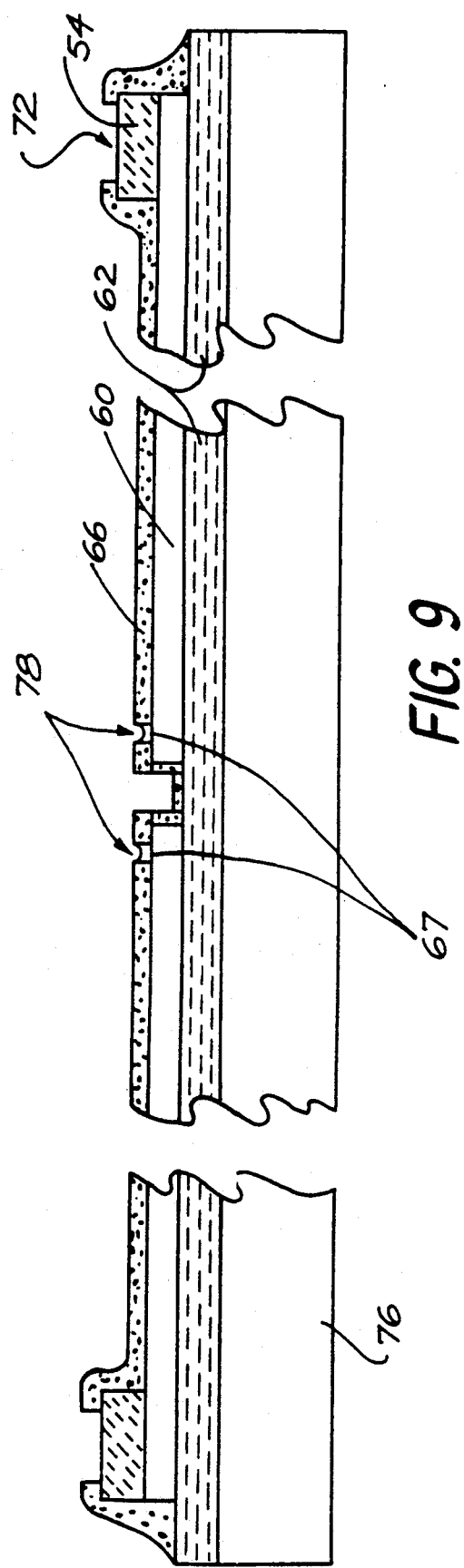
FIG. 9 shows a cross-sectional view of the chip of FIG. 8 taken along line A—A.
Figure 10:
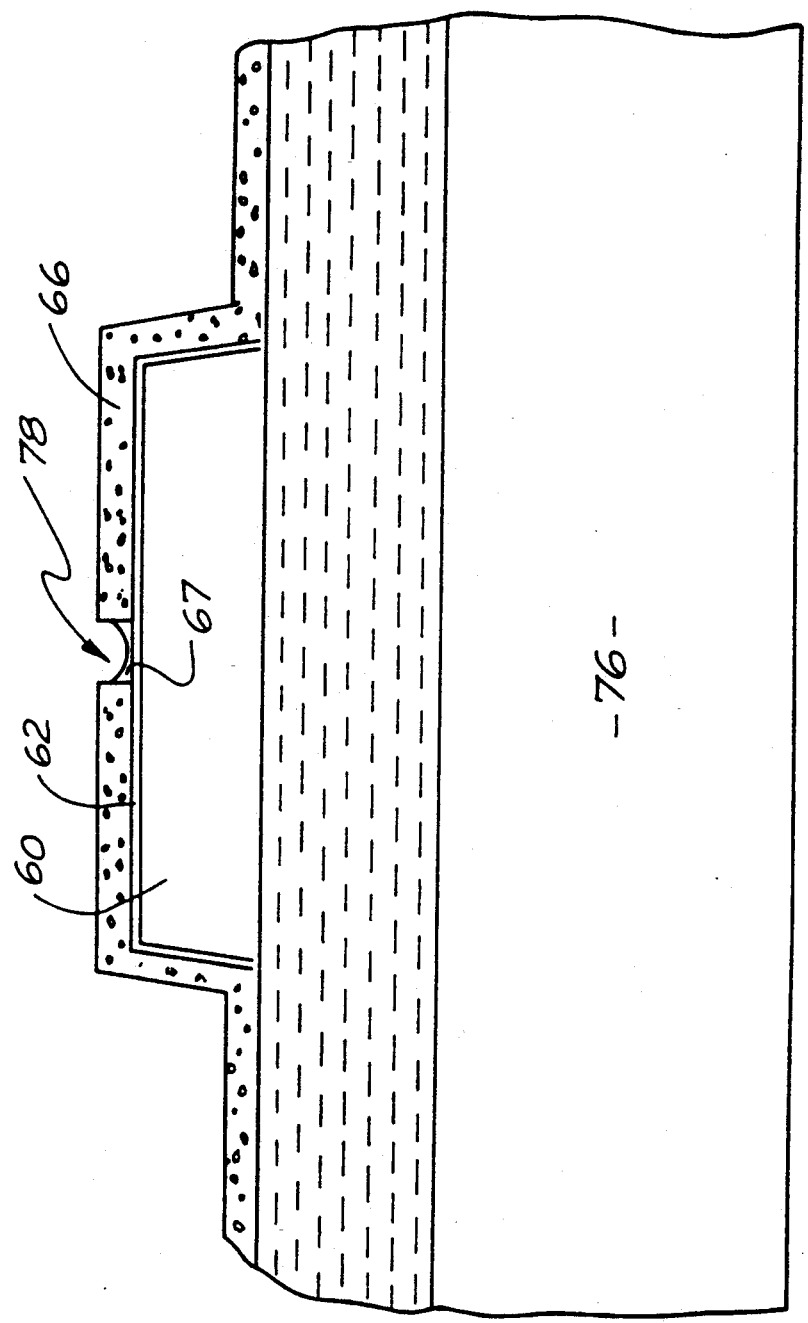
FIG. 10 shows a cross-sectional view of the chip of FIG. 8 taken along line B—B.

FIGS. 8-10 shows details of four mask levels necessary for fabrication with FIGS. 9 and 10 showing cross-sectional views taken along line A—A and B—B of FIG. 8 respectively. The chip size is 7 mm × 5 mm with the four mask levels required to pattern the layers given as Polysilicon, silicon dioxide, Aluminium and Nitride. These are shown as Polysilicon 60, silicon dioxide 62, Aluminium 64 and Nitride 66, electrode metallisation (gold, palladium or platinum) 67. The significance of these levels is as follows:

Polysilicon

Conducting polysilicon fingers 68 connecting each of the 10 pairs of sensing electrodes 70 to the respective aluminium bonding pads 72.

Silicon dioxide

A layer of deposited glass temporarily covering the tips of the polysilicon fingers 68 and designed to protect the pair of sensing electrodes 70. This layer is deposited after the formation of the sensing electrode metal and remains in during all subsequent operations including packaging. It is removed by hydrofluoric acid etch immediately prior to application of the lipidic biosensor film.

Nitride

A layer of deposited silicon nitride is the primary electrical insulation layer and covers the whole surface of the chip with the exception of windows over the pair of sensing electrodes 70 and bonding pads 72. Wire connecting leads 74 are provided to the bonding pads 72.

As is best shown in FIGS. 9 and 10 an electrode well 78 where the biosensor membrane is positioned is provided in each one of the each pair of electrodes 70.

Summary of the Process Steps

The starting material is a 6 inch diameter wafer of 100 single crystal silicon.

1. Grow 7500 angstroms of thermal oxide
2. Deposit 4000 angstroms of phosphorous doped silicon by low pressure chemical vapour deposition.
3. Carry out ophotolithographic processes to pattern polysilicon fingers, etch in plasma.
4. Oxidise polysilicon fingers to 300 angstroms thickness
5. Deposit 600 angstroms silicon nitride by low pressure chemical vapour deposition 6. Deposit 1200 angstroms of sputtered aluminium
7. Carry out photolithographic process to pattern aluminium bond pads—plasma etch
8. Carry out photolithographic process steps to pattern windows in nitride—plasma etch
9. Deposit gold platinum or palladium
10. Pattern electrode by lift off technique
11. Deposit 8000 angstroms glass (silox) by plasma enhanced chemical vapor deposition
12. Carry out photolithographic process steps to pattern silox—plasma etch
13. Saw into chips for packaging in moulding compound and chip carrier 76.
14. The protective silox should then be removed by etching with hydrofluoric acid and coated with lipid and biosensitive ion channels as described previously.

Many configurations are possible. The pattern shown is arranged as a general test unit which shows how electrodes can be either close packed or separated and how they can be used in various bridge configurations.

In one example the two close packed elements are used to provide a cross check on each other. The 10 pairs can then be used as individual biosensing elements to scan a surface of analyte using preamplifiers such as those given in FIGS. 6 and 7.

Another arrangement is to use them in a number of bridge circuits grouped so that some contain biosensitive ion channels, some contain ion channels which have not been modified for biosensitivity and the remainder contain only lipid material. Such grouped elements can be measured separately and compared after amplification; alternatively differential measurements can be carried out using bridges as per FIGS. 6.

To be practical the multiplexor circuitry requires that the active elements be attached to low impedance circuitry so that conventional three terminal bridges are not appropriate. It is also desirable for cost effectiveness that the high impedance element should not be located on the sensor chip. Arrangements which achieve this are given in FIG. 4 and use the amplifiers outlined in FIGS. 6 and 7.

Example 10

Synthesis of Cross-Linkable Moieties (i) Synthesis of p-Hydroxystyrene p-Hydroxyacetophenone was converted to 1-(p-acetoxyphenl) ethanol and then dehydrated using liquid phase dehydration in the presence of potassium acid sulfate to produce p-acetoxystyrene, according to the method of Corson et al. (*J. Org. Chem.*, 1958, 23, 544). p-Acetoxystyrene (1.6 g) was added to a stirred solution of potassium hydroxide (1.4 g) in water (14 ml) at 5 degrees Centigrade. Stirring was continued at 0.5 degrees Centigrade for 2 h. The mixture was then washed with ether, and the aqueous phase neutralized with saturated sodium hydrogen carbonate solution. The product was extracted into dichloromethane, the solution was dried over anhydrous calcium chloride and the solvent removed, to yield a cloudy oil (0.7 g) which solidified on standing to a waxy solid.

(ii) Synthesis of Methyl 11-(p-Vinylphenoxy)undecanoate

Hydrogen chloride gas was bubbled through a stirred solution of 11-bromoundecanoic acid (2.65 g) in methanol (20 ml) for 1 h at room temperature. The solvent was then removed and the residue in ether was washed with water, dried over anhydrous sodium sulfate and the solvent removed. The residual pale oil (2.8 g, 100%) was identified as methyl 11-bromoudecanoate.

This was converted to 11-(p-vinylphenoxy)undecanoic acid by the method of Hasegawa et al., *Polym. Bull.*, 1985, 14, 31.

(iii) Synthesis of 1-0-(11-(p-Vinylphenoxy)undecanoyl)-2-0-octadecylgycerol

The method of Hasegawa et al., *Poly. Bull.*, 1985, 14, 31, was followed, however, the condensation step was allowed to react for 5 days, and the product was chromatographed on silica gel, eluting with ether/light petroleum (1:3). The total product from 0.92 g 11-(p-vinylphenoxy) undecanoic acid was 1.25 g (66%).

Example 11

Synthesis of Linker Group for Attachment to Lipid or Ion Channels (i) 11-Chloro-3,6,9-trioxaundecan-1-ol 1,8-dichloro-3,6-dioxaoctane was prepared from triethylene glycol, thionyl chloride and pyridine according to the method of C. J. Pedersen (*J. Am. Chem. Soc.*, 1967, 89, 7017), b.p. 121°-122° C./15 mm Hg.

A solution of 1,8-dichloro-3,6-dioxaoctane (40 g) and potassium hydroxide (11.8 g) in ethylene glycol (100 ml) was stirred at 100° C. for 18 h. The mixture was then cooled, filtered and the residue washed with acetone (2×35 ml). The combined filtrate was then distilled to yield the product as a clear oil (13.5 g, 30%), b.p. 120°-122° C./0.2 mm Hg; I.r. (liquid film) 3430 cm$^{-1}$.

(ii) 11-Chloro-3,6,9-trioxaundec-1-yl succinate

A solution of 11-Chloro-3,6,9-trioxaundecan-1-01 (2.00 g), succinic anhydride (0.941 g), pyridine (0.10 ml), nd dimethylaminopyridine (0.02 g) in tetrahydrofuran (10 ml) was refluxed for 24 h. The mixture was cooled and the solvent was removed to yield the product as a clear oil (2.9 g, 100%). I.r (liquid film) 300 (b, Cl$_2$H), 1730 (C=O) cm$^{-1}$.

Example 12

Attachment of Linker Group to Lipid (i) 1-0-(11-(p-Vinylphenoxy)undecanoyl)-2-0-octadecyl -3-0-(11-chloro-3,6,9-trioxaundec-1-yl succinatoyl)glycerol 11-Chloro-3,6,9-trioxaundec-1-yl succinate (0.60 g) was dissolved in thionyl chloride (5 ml) and refluxed for 3 h. Excess thionyl chloride was removed, toluene (5 ml) was added and removed at 0.1 mm Hg to yield the carboxylic acid chloride as a pale yellow oil (0.64 g, 100%). I.r. (liquid film); 1785 (COCl), 1730 (C=O) cm$^{-1}$.

A solution of the carboxylic acid chloride (0.15 g) in tetrahydrofuran (0.5 ml) was added dropwise to a solution of 1-0-(11-(p-vinylphenoxy)undecanoyl)-2-0-octadecylglycerol (0.300 g) and pyridine (0.10 ml) in tetrahydrofuran (5 ml). The mixture was stirred at room temperature for 18 h and then poured onto water (75 ml). The combined chloroform extracts were washed with sulfuric acid (5%, 50 ml) and brine (50 ml), dried (MgSO$_4$) and evaporated. The crude product was chromatographed on silica, using ethyl acetate/light petroleum, 40:60 v/v/ as eluent, to yield the product as a clear oil, which solidified on standing (0.215 g, 49%). I.r. (liquid film) 1730 (C=O) cm$^{-1}$.

Hereafter this compound as referred to as linker lipid.

(ii)
1-0-(11-(p-Vinylphenoxy)undecanoyl)-2-0-octadecyl -3-0-acetoylglycerol

A mixture of 1-0-(11-(p-Vinylphenoxy)undecanoyl)-2-0-octadecylglycerol (0.20 g), redistilled acetic anhydride (3 ml) and pyridine (0.2 ml) was stirred at room temperature for 18 h. Excess acetic anhydride was distilled and the residue was taken up in chloroform (40 ml). The chloroform was washed with sodium hydrogen carbonate solution (5%, 2×50 ml), hydrochloride acid (5%, 50 ml) water (50 ml), dried (MgSO$_4$) and evaporated to yield the product as a colorless oil (0.16 g, 74%) which was homogeneous by t.l.c. IR 1735 cm$^{-1}$ (C=O).

Hereafter this compound is referred to as acetate lipid.

Example 13

Attachment of a Linker Group to Gramicidin A

A mixture of gramicidin (0.0633 g) 11-chloro-3,6,9-trioxaundec-1-yl succinate (0.032 g), dicyclohexyldiimide (0.021 g) and dimethylaminopyridine (0.020 g) in dichloromethane was stirred at room temperature for 24 h. The mixture was then washed with water (4×50 ml), dried (MgSO$_4$) and evaporated. The crude product was purified by preparative layer chromatography using dioxane as eluent to yield the gramicidin analogue (hereafter gramicidin R) as a white solid 0.30 g I.R. 1725 (CO$_2$) 1625 (CONH) cm$^{-1}$.

Example 14

Preparation, Isolation and Characterization of Fab Fragments

IgG antibodies were purified from ascites fluid by chromatography on Protein A to a single band on SDS polyacrylamide gel electrophoresis.

Fab$_2$ fragments were prepared from pure antibodies by pepsin digestion (1:100 enzyme: antibody weight ratio) for 30 minutes at pH 4.2 cation-exchange chromatography yielded the pure active Fab$_2$ fragments as established by the single band of 100,000 molecular weight mark on SDS polyacrylamide gel electrophoresis. Electrophoresis under reducing conditions showed a band at 25,000 molecular weight corresponding to the light chain and heavy chains of the two Fab' components of Fab$_2$.

Fab' were obtained from Fab$_2$ by modification of the method of Martin F. J. et al., *Biochemistry*, 1981, 20, 4229-38. Fab$_2$ were reduced with 20 mM dithiothreitol at pH 5.5 for 3 hours at room temperature. Dithiothreitol was removed by ultrafiltration using membranes with 30,000 molecular weight cut-off range. Fab' possessed comparable antigen binding activities to Fab$_2$ and gave a single band at the 50,000 and 25,000 molecular weight markers when SDS electrophoresis was carried out with non-reducing and reducing conditions, respectively. Fab' fragments were freshly prepared prior to linking to the amphophilic monolayer.

Fab$_2$ were radiolabelled with $^{125}$I to a specific activity of $10^8$ cmp/mg by chloramine T method. $^{125}$I Fab were incorporated into the unlabelled Fab$_2$ to a specific activity of $1 \times 10^4$ cpm per mg unlabelled Fab$_2$ and Fab fragments prepared as described above.

Covalent Attachment of Fab to Lipid and Binding Assay

Pepsin digestion of antibody and subsequent reduction of the resulting Fab$_2$ and Fab' fragments produces a single reactive thiol group at the carboxyl terminus of the Fab'. Coupling of this thiol group to the lipid molecule is achieved via the reaction with a terminal chlorine on polyethylene oxide attached to the polymerizable lipid molecule.

The monolayer of derivatized lipid was formed by spreading lipid in decane solution on an air-water interface in a Langmuir-Blodgett trough. The nylon peg substrate, previously treated to render surface hydrophobic, was dipped through the interface so that the hydrocarbon chains on the lipid interacted with the surface of the substrate.

The surface of the trough was cleaned of lipid before the substrate was quickly withdrawn and transferred to the Fab' solution.

The lipid-coated substrate was immersed into an aqueous solution of the Fab' at a concentration of 0.1 to 1.0 mg/ml of phosphate buffered saline buffer, pH 8. The reaction between the specific thiol on the Fab' and the chlorine of the lipid polyethylene oxide linker group was carried out for 3-20 hours at room temperature under N$_2$. $^{125}$I Fab' was used as a marker of the reaction as it was carried out on the lipid coated substrate.

The Fab' linked lipid coated substrate was then transferred to a microtitre well containing $^{125}$I-hCG at a concentration of 1 to 5 mg/ml, pH 7.4. The radioactivity of the entire substrate was measured after a fifteen immunoassay using the same amount of antibody in microtitre wells showed that the use of lipid-Fab coating yielded at least a 2-fold improvement in sensitivity.

The same treatment was applied to a pallandium-coated glass slide substrate, which showed at least a 3-fold increase in sensitivity compared to conventional immunoassay techniques. A coating of at least $10_{11}$ Fab molecules per cm$_2$ was achieved after incubation times longer than 10 hours as calculated from radioactivity measurements of $^{125}$I-Fab.

Use of 2 types of monoclonal Fab fragments, which bind to two different sides on the human chlorionic gonadotrophin (LCG), gave at least a 50% increase in sensitivity compared to using only one Fab.

Example 15

Synthesis of Gramicidin Dimer

A dimer of covalently linked head to head GA molecules having the sequence: HC-Trp-D-Leu-Trp-D-leu-Trp-D-Leu-Trp-D-Val-Val-D-Val  -Ala-D-Leu-Ala-Gly-Val-Gly-Ala-1-$^{13}$C-D-Leu-Ala-D-Val-Val-D-Val-Trp-D  -Leu-Trp-D-Leu-Trp-D-Leu-Trp-NHCH$_2$CH$_2$OH has been synthesized.

Chemicals

Side chain protected BOC-Trp(CHO) and all other BOC amino acids were purchased from Peptide Institute Inc. (Japan).

1-$^{13}$C-DL Leucine (1-$^{13}$C, 99%) was obtained from Cambridge Isotopes Laboratories (Woburn, Mass.). tBOC-Trp(CHO)OCH$_2$PAM resin (0.69 mmol/g) was obtained from Applied Biosystems.

Synthesis

BOC-1-$^{13}$-D-Leucine was synthesized, according to the procedure of Prasad et al., *Int. J. Peptide Protein Res.* 19, 1982, 162–171, with minor variations from the starting material of 1-$^{13}$C-DL Leucine.

The 1-$^{13}$C-D-Leu$_{18}$ dimer was synthesized by the solid phase method, using a 430A peptide synthesizer (Applied Biosystems) for the addition of all amino acids except the 1-$^{13}$ labelled D-Leu which was added manually.

The synthesis started with BOC-Trp(CHO)-OCH$_2$PAM resin (0.72 g) containing 0.5 mmol of BOC-Trp(CHO) esterified to 1% cross-linked polystyrene.

The first 6 cycles were single couplings of BOC amino acid with all remaining cycles being doubly coupled. First couplings were in DMF and recouplings were done with DCM as solvent.

Each amino acid was added with the following steps:
1. Resin washings in DCM.
2. Removal of the BOC group using 33% TFA in DCM for 80 sec., followed by 50% TFA/DCM for 18.5 minutes.
3. 3 DCM washes.
4. Neutralization with 10% diisoproyplethylamine (DIEA) in DMF for 2×1 min.
5. 5 DMF washes.
6. 26 min. coupling cycle in DMF via amino acid anhydride (2 fold excess of anhydride) using 2 mmol BOC amino acid and dicyclohexylcarbodiimide (DCC).
7. 4 DCM washes.

Recouple cycle.
1. 1 wash in coupling solvent (DCM).
2. 10% DIEA in DCM for 30 sec.
3. 5 DCM washes.
4. Recoupling in DCM 30 minutes.
5. 1 DMF wash.
6. 5 DCM washes.

The 1-$^{13}$C-labelled D-Leu was added to the peptide manually. The resin was removed from the synthesizer reaction vessel after step 5 (neutralization and washings) of this cycle.

One equivalent (0.5 mmol) of BOC 1-$^{13}$C-D-Leu was added in 2 ml DCM and stirred for 10 min. One equivalent of DCC in 2 ml of DMF was then added and allowed to react at room temperature overnight.

The resin was then returned to the synthesizer where it was washed and then recoupled with unlabelled BOC-D-Leu using the above recoupling cycle.

Resin samples were taken on completion of each cycle in the synthesis to determine the extent of coupling using quantitative ninhydrin assay (Sarin et al., *Analytical Biochemistry*, 117, 147–157, 1981). Each reaction was 99% complete.

The completed peptide was removed from the resin by reaction with ethanolamine to give the terminal ethanolamine moiety, followed by de-BOCing and formulation reactions as described in Prasad et al. (1982).

Initial purification of the crude peptide was obtained by filtration in methanol on a 100 cm × 3.2 cm id column of Sephadex LH20 Pharmacia).

Fractions collected from this column were analyzed by reversed phase HPLC on a radial compression column (8 mm id × 10 cm) using either an isocratic aq MeOH solvent (92% MeOH) or a 92% aq MeOH to 100% MeOH gradient.

Analytical TLC's were done on silica gel plates (Merck Kieselgel 60 F-254) using solvents.

Chloroform/MeOH/glacial acetic acid 90:10:3 and CHCl$_3$/MeOH/H$_2$O 65:25:4 and bands were visualized by ultraviolet light.

The following examples relate to a biosensor fabricated from an amphiphile-ion channel surface attached to a metal electrode. Receptor modules are covalently linked to the amphiphile-ion channel coating. The binding of the ligand to the receptor molecules act as the gating mechanism, changing the conductance of the ion channel. The gating mechanism is related to ion channel concentration and receptor concentration, as exemplified by the following.

Example 16

Synthesis of a Biosensor

A lipid gramicidin surface was prepared on a palladium-coated glass electrode as described in Example 5. The first monolayer consisted of dodecane-thiol:gramicidin (ratio 30 to 10 and the second monolayer consisted of acetate lipid:gramicidin R (at a ratio of 100 to 1). The formation of the gramicidin R was as described in Example 13.

The electrode was then incubated in a Fab solution consisting of Fab prepared from two monoclonal antibodies to hCG which bind to two distinct site son the hCG molecule. The ration of the two types of Fab was 1:1. Total concentration of Fab was 0.1 to 1.0 mg/ml of phosphate buffered saline, pH 8. The electrode was incubated at room temperature for 3 to 19 hours. The electrical impedance of the electrode was measured through a frequency range of 1 millihertz to 5 kilhertz, using a three electrode system, a "Solartron 1250 FRA" impedance analyzer and an electro-chemical interface amplifier. Impedance of the lipid gramicin bilayer was $10^{4.95}$ ohms at 10 millihertz corresponding to $1.6 \times 10^4$ conducting gramicidin channels. (All estimates of number of conducting channel are based on the gramicidin resistance in black lipid membranes of $10^{11}$ ohms/channel.)

Optimal incubation time was twelve hours in the Fab solution which gave an increased impedance measurement of $10^{6.15}$ ohms at 10 millihertz arising from $5.9 \times 10^4$ conducting gramicin channels (measured at 1 millihertz). Washing the electrode in running water and leaving in distilled water for 48 hours did not change the impedance of the electrode.

The electrode was incubated with hCG in 0.1M NaCl for 15 minutes at 37° C. After washing with distilled water, the electrode was returned to the 0.1M NaCl call and its impedance was measured. An incubation time of 12 hours in an Fab solution was found to give the most sensitive change in impedance upon hCG binding. 0.96 nanograms hCG per ml gave an increased impedance of $10^{6.20}$ ohms at 10 gramicidin channels, measured at 1 millihertz.

Washing the electrode with distilled water or ethanol did not change the impedance. Soaking the electrode in distilled water or 0.1M NaCl for 24 hours also did not change the impedance of the electrode.

Example 17

Palladium-Coating Glass Electrodes were coated using the method described in Example 16. The first monolayer is as described in Example 16, and the second monolayer consisted of total lipid:gramicidin at a ratio of 100:1, where the total lipid consisted of acetate lipid: linker lipid (see Examples 10 to 12) at a ratio of 100:1.

The impedance of the electrode was measured as described in Example 16. The electrode was incubated in Fab solution for 5 to 19 hours as described in Example 16. A lipid-Fab electrode measured after 5.5 hours incubation in the Fab solution gave an impedance of $10^{5.4}$ ohms at 10 millihertz corresponding to $1.9 \times 10^5$ conducting gramicin channels, compared to a lipid-gramicidin only bilayer impedance of $10^{4.6}$ ohms at 10 millihertz.

hCG was incubated with the Fab covered lipid-gramicidin coated electrode as described in Example 16. The incubation time of 5.5 hours in the Fab solution was found to give the most sensitive change in impedance upon hCG binding. An impedance of $10^{5.55}$ ohms at 10 millihertz corresponding to $1.2 \times 10^5$ conducting gramicidin channels was measured after addition of 0.96 nanograms hCG per ml. A further addition of hCG to a total concentration of 2.56 nanograms per ml increased the impedance in the electrode to $10^{5.93}$ ohms at 10 millihertz corresponding to $5.6 \times 10^5$ conducting gramicidin channels.

Another electrode with the same coating as described above gave an impedance measurement of $10^{5.8}$ ohms at 10 millihertz with 5.5 hours Fab incubation and an impedance measurement of $10^{6.15}$ ohms at 10 millihertz with addition of 0.96 nanograms hCG per ml. As a control, addition of the same amount of bovine serum albumin instead of hCG (i.e., $1092 \times 10^{-14}$ mol per ml) gave an impedance measurement of $10^{5.80}$ ohms at 10 millihertz, equivalent to the lipid-Fab coated electrode without hCG.

We claim:

1. A biosensor comprising a plurality of discrete, substantially identical membranes, each membrane including at least one gated ion channel, the conductance of each membrane being measurable independently of the conductance of the other membranes, each of said membranes comprising a closely packed array of self-assembling amphophilic molecules, at least one dedicated electrode provided on one side of the membrane which cooperates with an electrode on the other side of the membrane to enable the application of an electrical potential across the membrane, the at least one gated ion channel having a conductance which is dependent upon the electric potential applied across the membrane.

2. A biosensor as claimed in claim 1 in which the ion channel is modified by incorporation or removal of polar, dipolar or polarisable groups.

3. A biosensor as claimed in claim 1 in which at least one dedicated electrode is provided on one side of each membrane which cooperates with an electrode on the other side of the each membrane to enable the application of an electric potential across the membrane, the plurality of membranes being multiplexed by multiplexing the signal applied to or measured from the respective discrete electrodes.

4. A biosensor comprising a plurality of discrete substantially identical membranes, each membrane including at least one gated ion channel, each of said membranes comprising a closely packed array of self-assembling amphophilic molecules, the conductance of each of said membranes being measurable independently of the conductance of the other membranes, at least one dedicated electrode provided on one side of the membrane which cooperates with an electrode on the other side of the membrane to enable the application of an electric potential across the membrane, the signal applied to or measured from the discrete membranes.

5. A biosensor as claimed in claim 1 in which the ion channel is selected from the group consisting of peptides capable of forming helices and aggregates thereof, podands, coronands and cyptands.

6. A biosensor as claimed in claim 5 in which the ion channel is a peptide capable of forming a helix or aggregates thereof.

7. A biosensor as claimed in claim 6 in which the ion channel is a peptide which forms a $\beta$ helix.

8. A biosensor as claimed in claim 7 in which the ion channel is gramicidin or analogs thereof.

9. A biosensor as claimed in claim 8 in which the ion channel is gramicidin A or analogs thereof.

10. A biosensor as claimed in claim 1 in which the gates ion channel can diffuse laterally within the lipid membrane.

11. A biosensor as claimed in claim 1 in which the conductance of each lipid membrane is measured by means of a high impedance address lines, a separate address line being provided to each lipid membrane and/or multiplexing the membrane.

12. A biosensor as claimed in claim 11 in which the conductance of each lipid membrane is measured by multiplexing the membranes.

13. A biosensor as claimed in claim 12 in which the membranes are serially multiplexed.

14. A biosensor as claimed in claim 12 in which the conductance measurements are made using multiplex lines of low impedance and at least one current sensing line.

15. A biosensor as claimed in claim 14 in which there is one current sensing line.

16. A biosensor as claimed in claim 1 in which the conductance of each membrane is measured by means of switching between low impedance address lines each of which supplies a signal which is measured either by a single current sensor common to all the address lines or by a number of current sensors which are electrically isolated from each other and which measure groups of address lines.

17. A biosensor as claimed in claim 1 in which the conductance of each membrane is measured by means of switching between high impedance address lines each of which supply a signal which is measured either by a single current sensor common to all the address lines or by a number of current sensors which are electrically isolated from each other and which measure groups of address lines.

18. A biosensor as claimed in claim 11 which the gated ion channels are field effect ion channels.

19. A biosensor as claimed in claim 18 in which the plurality of discrete membranes are arranged in a two dimensional array.

20. A biosensor as claimed in claim 19 in which the multiplex lines are driven from a complex signal such that in the two dimensional array each address line in one dimension has signal components which are cross modulated with signals from address lines in the other dimension by the field effect ion channel 21. A biosensor as claimed in claim 1 in which the conductance of each lipid membrane is measured by means of a high impedance address line either by using a separate amplifier for each membrane or by switching one amplifier between each membrane or by switching a number of amplifiers between a number of membranes such that each membrane is measured.

22. A biosensor as claimed in claim 4 in which the ion channel is selected from the group consisting of peptides capable of forming helices and aggregates thereof, podands, coronands and cryptands.

23. A biosensor as claimed in claim 22 in which the ion channel is a peptide capable of forming a helix or aggregates thereof.

24. A biosensor as claimed in claim 23 in which the ion channel is a peptide which forms a $\beta$ helix.

25. A biosensor as claimed in claim 24 in which the ion channel is gramicidin or analogs thereof.

26. A biosensor as claimed in claim 25 in which the ion channel is gramicidin A or analogs thereof.

27. A biosensor as claimed in claim 4 in which the grated ion channel can diffuse laterally within the lipid membrane.

28. A biosensor as claimed in claim 4 in which the conductance of each lipid membrane is measured by means of a high impedance address lines, a separate address line being provided to each lipid membrane and/or multiplexing the membranes.

29. A biosensor as claimed in claim 28 in which the conductance of each lipid membrane is measured by multiplexing the membranes.

30. A biosensor as claimed in claim 29 in which the membranes are serially multiplexed.

31. A biosensor as claimed in claim 29 in which the conductance measurements are made using multiplex lines of low impedance and at least one current sensing line.

32. A biosensor as claimed in claim 31 in which there is one current sensing line.

33. A biosensor as claimed in claim 21 in which the conductance of each membrane is measured by means of switching between low impedance address lines each of which supplies a signal which is measured either by a single current sensor common to all the address lines or by a number of current sensors which are electrically isolated from each other and which measure groups of address lines.

34. A biosensor as claimed in claim 4 in which the conductance of each membrane is measured by means of switching between high impedance address lines each of which supply a signal which is measured either by a single current sensor common to all the address lines or by a number of current sensors which are electrically isolated from each other and which measure groups of address lines.

35. A biosensor as claimed in claim 4 in which the gated ion channels are field effect ion channels.

36. A biosensor as claimed in claim 35 in which the plurality of discrete membranes are arranged in a two dimensional array.

37. A biosensor as claimed in claim 36 in which the multiplex lines are driven from a complex signal such that in the two dimensional array each address line in one dimension has signal components which are cross modulated with signals from address lines in the other dimension by the field effect ion channel.

38. A biosensor as claimed in claim 4 in which the conductance of each lipid membrane is measured by means of a high impedance address line either by using a separate amplifier for each membrane or by switching one amplifier between each membrane or by switching a number of amplifiers between a number of membranes such that each membrane is measured.

* * * * *